US006550472B2

(12) United States Patent
Litherland et al.

(10) Patent No.: US 6,550,472 B2
(45) Date of Patent: Apr. 22, 2003

(54) DEVICES AND METHODS FOR NEBULIZING FLUIDS USING FLOW DIRECTORS

(75) Inventors: Craig Litherland, Cupertino, CA (US); Kamran Behzadian, Sunnyvale, CA (US)

(73) Assignee: Aerogen, Inc., Sunnyvale, CA (US)

(*) Notice: Subject to any disclaimer, the term of this patent is extended or adjusted under 35 U.S.C. 154(b) by 0 days.

(21) Appl. No.: 09/809,783

(22) Filed: Mar. 16, 2001

(65) Prior Publication Data

US 2002/0129812 A1 Sep. 19, 2002

(51) Int. Cl.[7] .............................................. A61M 11/00

(52) U.S. Cl. ........................... 128/200.18; 128/200.14; 128/200.16; 239/338; 239/102.2; 239/499; 239/509

(58) Field of Search ........................ 128/200.14, 200.16, 128/200.18, 203.12, 203.24; 239/338, 102.2, 499, 509

(56) References Cited

U.S. PATENT DOCUMENTS

| | | | | |
|---|---|---|---|---|
| 2,101,304 A | | 12/1937 | Wright | 120/50 |
| 2,158,615 A | | 5/1939 | Wright | 120/50 |
| 2,187,528 A | | 1/1940 | Wing | 120/50 |
| 2,223,541 A | | 12/1940 | Baker | 120/50 |
| 2,266,706 A | | 12/1941 | Fox et al. | 128/173 |
| 2,283,333 A | | 5/1942 | Martin | 120/50 |
| 2,292,381 A | | 8/1942 | Klagges | 120/50 |
| 2,360,297 A | | 10/1944 | Wing | 120/52 |
| 2,375,770 A | | 5/1945 | Dahlberg | 120/52 |
| 2,404,063 A | | 7/1946 | Healy | 120/51 |
| 2,430,023 A | | 11/1947 | Longmaid | 120/52 |
| 2,474,996 A | | 7/1949 | Wallis | 120/52 |
| 2,512,004 A | | 6/1950 | Wing | 120/52 |
| 2,521,657 A | | 9/1950 | Severy | 120/50 |
| 2,681,041 A | | 6/1954 | Zodtner et al. | 120/50 |
| 2,779,623 A | | 3/1957 | Eisenkraft | 299/1 |
| 2,935,970 A | | 5/1960 | Morse et al. | 120/52 |
| 3,411,854 A | | 11/1968 | Rosler et al. | 401/227 |
| 3,558,052 A | | 1/1971 | Dunn | 293/3 |
| 3,738,574 A | | 6/1973 | Guntersdorfer et al. | 239/102 |
| 3,790,079 A | | 2/1974 | Berglund et al. | 239/3 |
| 3,804,329 A | | 4/1974 | Martner | 239/4 |
| 3,812,854 A | | 5/1974 | Michaels et al. | 128/194 |
| 3,828,773 A | * | 8/1974 | Buch et al. | 128/200.16 |
| 3,950,760 A | | 4/1976 | Ilse-dore Stromberger et al. | 346/140 |
| 3,958,249 A | | 5/1976 | DeMaine et al. | 346/1 |
| 3,983,740 A | | 10/1976 | Danel | 73/12 |

(List continued on next page.)

*Primary Examiner*—Aaron J. Lewis
*Assistant Examiner*—Mital Patel
(74) *Attorney, Agent, or Firm*—Townsend and Townsend and Crew LLP

(57) ABSTRACT

A device for nebulizing a fluid is supplied which has a flow director. The flow director helps to direct any bubbles formed by the nebulizing device away from the nebulizing device. The nebulizing device has a vibrating element with apertures through which the fluid is dispensed. A dispensing chamber is defined between the flow director and the vibrating element. The dispensing chamber has an inlet which is positioned below an outlet so that bubbles naturally migrate up and away from the vibrating element.

26 Claims, 11 Drawing Sheets

U.S. PATENT DOCUMENTS

| | | | |
|---|---|---|---|
| 4,005,435 A | 1/1977 | Lundquist et al. | 346/1 |
| 4,119,096 A | 10/1978 | Drews | 128/194 |
| 4,159,803 A | 7/1979 | Cameto et al. | 239/102 |
| 4,226,236 A | 10/1980 | Genese | |
| 4,240,081 A | 12/1980 | Devitt | 346/75 |
| 4,261,512 A | 4/1981 | Zierenberg | 239/102 |
| 4,268,460 A | 5/1981 | Boiarski | 261/1 |
| 4,294,407 A | 10/1981 | Reichl et al. | 239/102 |
| 4,300,546 A | 11/1981 | Kruber | 128/200 |
| 4,301,093 A | 11/1981 | Eck | 261/1 |
| 4,334,531 A | 6/1982 | Reichl et al. | 128/200.14 |
| 4,336,544 A | 6/1982 | Donald et al. | 346/1.1 |
| 4,338,576 A | 7/1982 | Takahashi et al. | 331/67 |
| 4,368,476 A | 1/1983 | Uehara et al. | 346/140 R |
| 4,389,071 A | 6/1983 | Johnson, Jr. et al. | 299/14 |
| 4,408,719 A | 10/1983 | Last | 239/102 |
| 4,431,136 A | 2/1984 | Janner et al. | 239/102 |
| 4,454,877 A | 6/1984 | Miller et al. | 128/200.21 |
| 4,465,234 A | 8/1984 | Maehara et al. | 239/102 |
| 4,474,251 A | 10/1984 | Johnson, Jr. | 175/67 |
| 4,474,326 A | 10/1984 | Takahashi | 239/102 |
| 4,475,113 A | 10/1984 | Lee et al. | 346/1.1 |
| 4,479,609 A | 10/1984 | Maeda et al. | 239/102 |
| 4,530,464 A | 7/1985 | Yamamoto et al. | 239/102 |
| 4,533,082 A | 8/1985 | Maehara et al. | 239/102 |
| 4,539,575 A | 9/1985 | Nilsson | 346/140 R |
| 4,544,933 A | 10/1985 | Heinzl | 346/140 R |
| 4,546,361 A | 10/1985 | Brescia et al. | 346/140 R |
| 4,550,325 A | 10/1985 | Viola | 346/140 R |
| 4,591,883 A | 5/1986 | Isayama | 346/140 R |
| 4,593,291 A | 6/1986 | Howkins | 346/1.1 |
| 4,605,167 A | 8/1986 | Maehara | 239/102 |
| 4,620,201 A | 10/1986 | Heinzl et al. | 346/140 R |
| 4,628,890 A | 12/1986 | Freeman | 123/593 |
| 4,632,311 A | 12/1986 | Nakane et al. | 239/102 |
| 4,659,014 A | 4/1987 | Soth et al. | 239/102.2 |
| 4,681,264 A | 7/1987 | Johnson, Jr. | 239/589.1 |
| 4,702,418 A | 10/1987 | Carter et al. | 239/101 |
| 4,722,906 A | 2/1988 | Guire | |
| 4,753,579 A | 6/1988 | Murphy | 417/322 |
| 4,790,479 A | 12/1988 | Matsumoto et al. | 239/102.2 |
| 4,793,339 A | 12/1988 | Matsumoto et al. | 128/200.16 |
| 4,796,807 A | 1/1989 | Bendig et al. | 239/102.2 |
| 4,799,622 A | 1/1989 | Ishikawa et al. | 239/102.2 |
| 4,826,759 A | 5/1989 | Guire | |
| 4,828,886 A | 5/1989 | Hieber | 427/422 |
| 4,850,534 A | 7/1989 | Takahashi et al. | 239/102.2 |
| 4,865,006 A | 9/1989 | Nogi et al. | 123/590 |
| 4,877,989 A | 10/1989 | Drews et al. | 310/323 |
| 4,888,516 A | 12/1989 | Daeges et al. | 310/323 |
| 4,968,299 A | 11/1990 | Ahlstrand et al. | |
| 4,973,493 A | 11/1990 | Guire | |
| 4,976,259 A | 12/1990 | Higson et al. | |
| 4,979,959 A | 12/1990 | Guire | |
| 4,994,043 A | 2/1991 | Ysebaert | |
| 5,002,582 A | 3/1991 | Guire et al. | |
| 5,021,701 A | 6/1991 | Takahashi et al. | 310/345 |
| 5,063,396 A | 11/1991 | Shiokawa et al. | 346/140 R |
| 5,063,922 A | 11/1991 | Hakkinen | 128/200.16 |
| 5,073,484 A | 12/1991 | Swanson et al. | |
| 5,076,266 A | 12/1991 | Babaev | 128/200.36 |
| 5,080,649 A | 1/1992 | Vetter | |
| 5,086,785 A | 2/1992 | Gentile et al. | |
| 5,115,803 A | 5/1992 | Sioutas | 128/200.23 |
| 5,134,993 A * | 8/1992 | van der Linden et al. | 128/200.14 |
| 5,139,016 A | 8/1992 | Waser | 128/200.16 |
| 5,140,740 A | 8/1992 | Weigelt | |
| 5,152,456 A | 10/1992 | Ross et al. | 239/102.2 |
| 5,157,372 A | 10/1992 | Langford | |
| 5,164,740 A | 11/1992 | Ivri | 346/1.1 |
| 5,170,782 A | 12/1992 | Kocinski | 128/200.16 |
| 5,186,164 A | 2/1993 | Raghuprasad | |
| 5,186,166 A | 2/1993 | Riggs et al. | |
| 5,198,157 A | 3/1993 | Bechet | 264/9 |
| 5,217,492 A | 6/1993 | Guire et al. | |
| 5,258,041 A | 11/1993 | Guire et al. | |
| 5,261,601 A | 11/1993 | Ross et al. | 239/102.2 |
| 5,263,992 A | 11/1993 | Guire | |
| 5,297,734 A | 3/1994 | Toda | 239/102.2 |
| 5,299,739 A | 4/1994 | Takahashi et al. | 239/102.2 |
| 5,309,135 A | 5/1994 | Langford | |
| 5,312,281 A | 5/1994 | Takahashi et al. | 446/25 |
| 5,320,603 A | 6/1994 | Vetter et al. | |
| 5,347,998 A | 9/1994 | Hodson et al. | 128/200.23 |
| 5,414,075 A | 5/1995 | Swan et al. | |
| 5,415,161 A | 5/1995 | Ryder | 128/200.23 |
| 5,449,502 A * | 9/1995 | Igusa et al. | 134/198 |
| 5,452,711 A | 9/1995 | Gault | |
| 5,477,992 A | 12/1995 | Jinks et al. | 222/402.16 |
| 5,487,378 A | 1/1996 | Robertson et al. | 128/200.16 |
| 5,497,944 A * | 3/1996 | Weston et al. | 128/200.14 |
| 5,512,329 A | 4/1996 | Guire | |
| 5,512,474 A | 4/1996 | Clapper et al. | |
| 5,515,841 A | 5/1996 | Robertson et al. | 128/200.16 |
| 5,515,842 A | 5/1996 | Ramseyer et al. | |
| 5,518,179 A | 5/1996 | Humberstone et al. | 239/102.2 |
| 5,533,497 A | 7/1996 | Ryder | 128/200.21 |
| 5,549,102 A * | 8/1996 | Lintl et al. | 128/200.18 |
| 5,563,056 A | 10/1996 | Swan et al. | |
| 5,579,757 A | 12/1996 | McMahon et al. | 128/200.21 |
| 5,586,550 A | 12/1996 | Ivri et al. | 128/200.16 |
| 5,637,460 A | 6/1997 | Swan et al. | |
| 5,654,162 A | 8/1997 | Guire et al. | |
| 5,654,460 A | 8/1997 | Rong | |
| 5,665,068 A | 9/1997 | Takamura | |
| 5,692,644 A | 12/1997 | Gueret | |
| 5,707,818 A | 1/1998 | Chudzik et al. | |
| 5,714,360 A | 2/1998 | Swan et al. | |
| 5,714,551 A | 2/1998 | Bezwada et al. | |
| 5,718,222 A | 2/1998 | Lloyd et al. | |
| 5,744,515 A | 4/1998 | Clapper | |
| 5,758,637 A | 6/1998 | Ivri et al. | 128/200.16 |
| 5,823,179 A * | 10/1998 | Grychowski et al. | 128/200.14 |
| 5,893,515 A | 4/1999 | Hahn et al. | |
| 5,938,117 A | 8/1999 | Ivri | 239/4 |
| 5,970,974 A * | 10/1999 | Van Der Linden et al. | 128/200.14 |
| 6,012,450 A | 1/2000 | Rabsamen | |
| 6,014,970 A | 1/2000 | Ivri et al. | |
| 6,085,740 A | 7/2000 | Ivri et al. | |
| 6,223,746 B1 * | 5/2001 | Jewett et al. | 128/200.14 |

* cited by examiner

DEVICES AND METHODS FOR NEBULIZING FLUIDS USING FLOW DIRECTORS

CROSS REFERENCE TO RELATED APPLICATIONS

This invention is related to U.S. patent application Ser. No. 09/614,306, filed Jul. 12, 2000, the complete disclosure of which is herein incorporated by reference.

BACKGROUND OF THE INVENTION

The present invention is directed to methods and devices for nebulizing fluids. In a specific application of the present invention, the device is used to nebulize fluids for delivery to the lungs. Although the present invention is particularly useful for nebulizing fluids for inhalation, it is understood that the present invention may be used for nebulizing fluids in other fields and for other purposes.

SUMMARY OF THE INVENTION

In a first aspect of the present invention, a nebulizing device is provided which has at least two nebulizing elements. In a preferred embodiment, the nebulizing element has a vibrating element with a plurality of apertures. The vibrating element is preferably a relatively stiff element, such as a rigid dome-shaped element, but may be any other suitable structure. The vibrating elements are vibrated to expel fluid through the apertures.

The device may be operated to provide independent delivery of two different fluids. In a specific application of the present invention for nebulizing liquids for inhalation, the first fluid may contain an immune modulator or a mucolytic, such as alpha domase, and the second fluid could contain an antibiotic, such as an aminoglycocide like tobramicin, or quinolone, pentamidine, or an antifungal such as amphotericin B. Another application for the device is for the first fluid to contain a short acting beta agonist and the second fluid to contain a corticosteroid. The beta agonist provides symptomatic relief and the corticosteroid treats the underlying immune reaction. The beta agonist may be any suitable beta agonist such as albuterol. These drugs complement one another in the treatment of asthma. Other combinations of drugs may be delivered with the device which relate to the same ailment or to different ailments.

The first and second fluids may also be delivered in the same breath. In one aspect, the first fluid may be delivered earlier than the second fluid. For example, the first fluid could contain a bronchodilator which opens the lungs for delivery of the second fluid. Alternatively, the second fluid could be a bronchorestrictor delivered after the first fluid to help retain the first fluid in the lungs. Of course, any combinations of liquids may be delivered as the first and second fluids and the examples given are merely illustrative.

Although the device may be operated to deliver two or more fluids, the device may be used to deliver a single fluid. When delivering only one fluid, the combination of nebulizers provides enhanced flow. For example, the nebulizing elements may together be used to deliver 40–300 microliters, more preferably 100–250 microliters, in one breath. Stated another way, the nebulizing elements are used to deliver at least 100 microliters and more preferably at least 200 microliters of fluid in one breath by the user. Stated still another way, the device delivers the preferred amounts in no more than four seconds of operating time. The first and second nebulizers also provide the ability to provide relatively large increases and decreases in fluid flow rate by simply activating or de-activating one or more of the nebulizers. Of course, the flow rate of each of the nebulizers may be adjusted by changing the power or frequency of operation.

In another aspect of the present invention, the nebulizer may also instruct or permit the user to inhale a set number of doses over a period of time. For example, the device may permit and/or instruct the user to inhale six doses of the first fluid, such as a beta agonist, per day and only two doses of the second fluid, such as a corticosteroid. The control system may also permit a set number of doses of one of the fluids in relation to the amount of the other fluid delivered. In this manner, the relative amounts of the two fluids can be regulated.

The present invention is also directed to a flow director which may be used with the nebulizing devices of the present invention. As mentioned above, the present invention is directed to nebulizing fluids for inhalation but may be used for any other purpose. The nebulizing device has a vibrating element with a plurality of apertures therein. The vibrating element has a front side and a back side with the plurality of apertures extending between the front and back sides. A flow director is positioned adjacent to the back side of the vibrating element and defines a dispensing chamber therebetween. The flow director provides various advantages as described below. One advantage of the flow director is that the flow director can help to remove and reduce bubbles produced in the dispensing chamber.

In a preferred embodiment, an outlet chamber receives bubbles that may form in the dispensing chamber. The outlet chamber may have an active feature to accelerate bubble collapse, such as a source of heat, cold or electrical energy, or a passive feature, such as a protrusion, surface features or a coating. The inlet is preferably positioned below the outlet so that bubbles naturally migrate upward toward the outlet. In a preferred embodiment, the flow director is positioned 0.003–0.015 inch, and more preferably 0.003–0.030 inch from the back side of the vibrating element to form a relatively small volume in the dispensing chamber. The dispensing chamber preferably holds 2–40 micoliters and more preferably 2–30 microliters. The relatively small size of the dispensing chamber and proximity of the flow director together and independently may tend to inhibit bubble formation and prevent an accumulation of bubbles.

These and other advantages and features will become apparent with the following description of the preferred embodiments, drawings and claims.

DESCRIPTION OF THE SPECIFIC EMBODIMENTS

Figure 1:
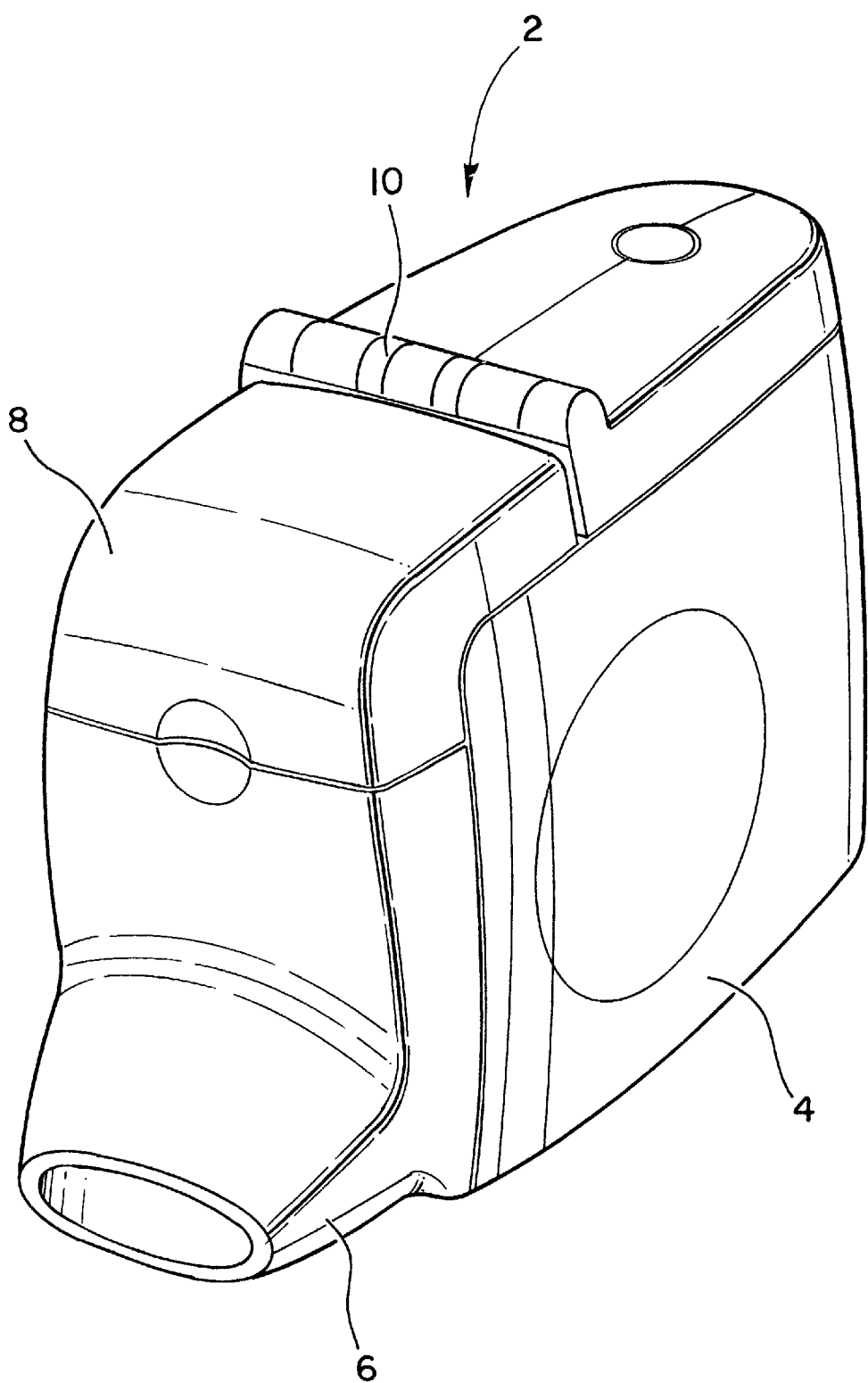
FIG. 1 is an isometric view of a device in accordance with the present invention.
Figure 2:
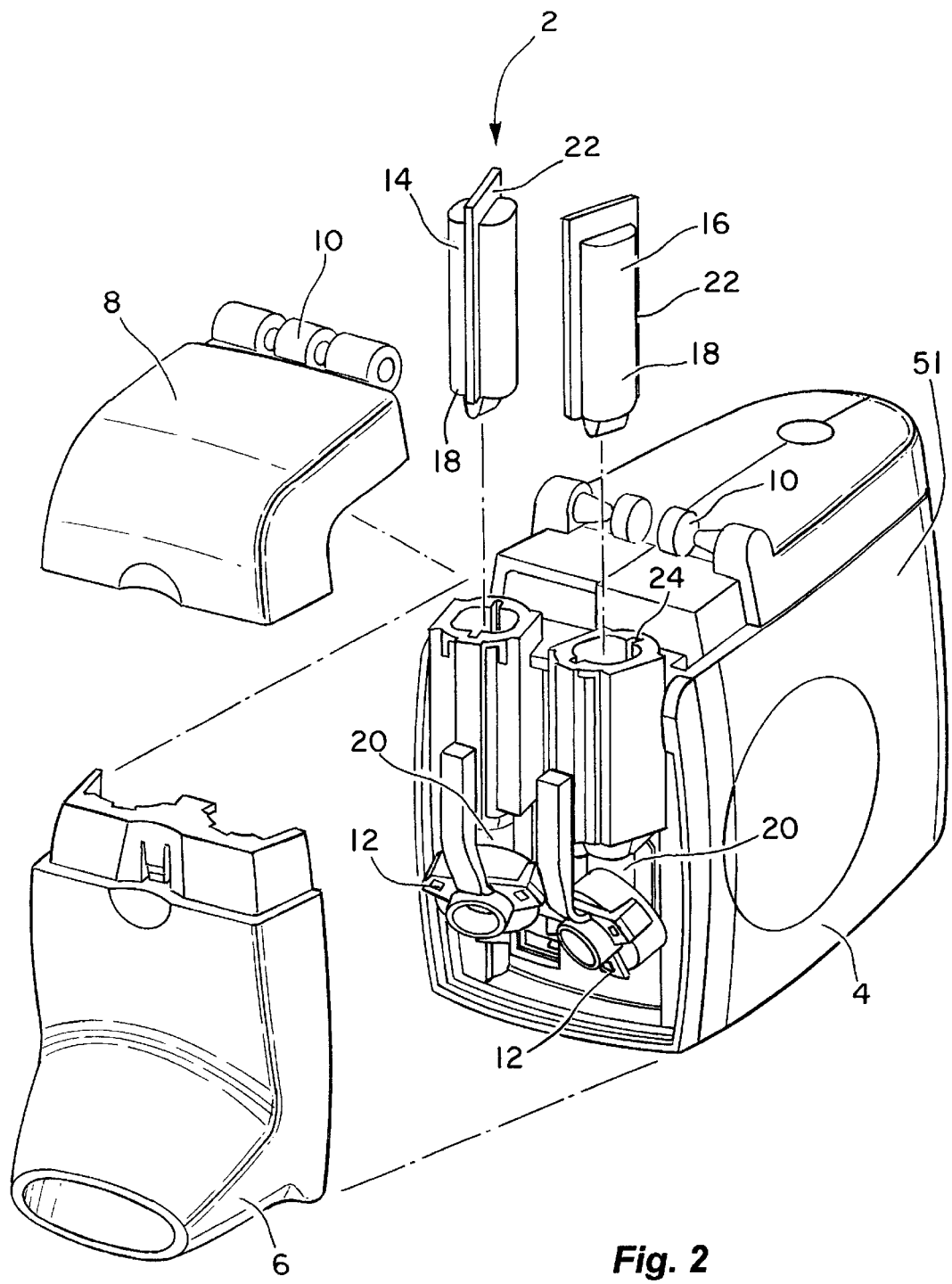
FIG. 2 shows the device with a door and mouthpiece removed to expose internal components of the device.
Figure 3:
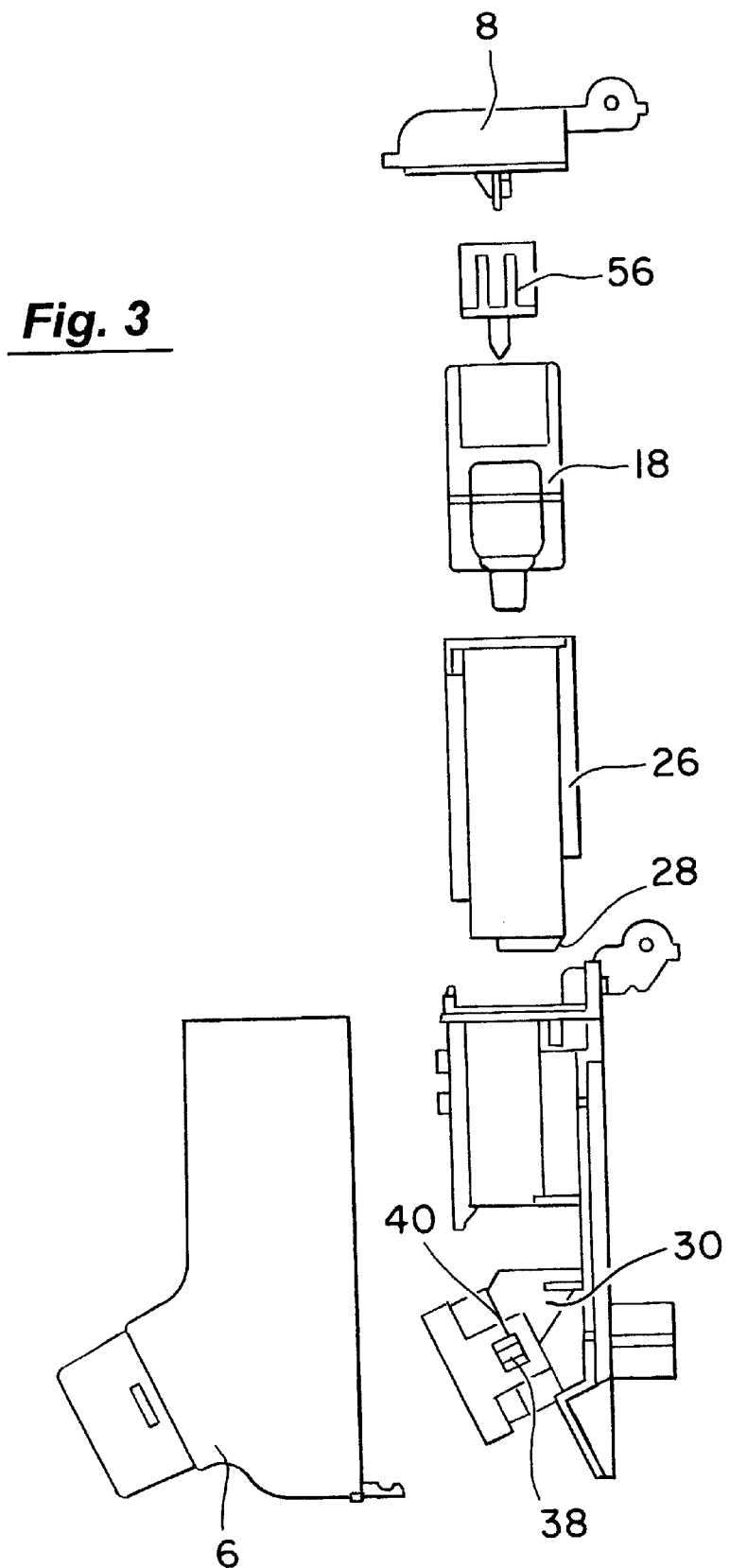
FIG. 3 is a side view of another fluid delivery system for the device.
Figure 4:
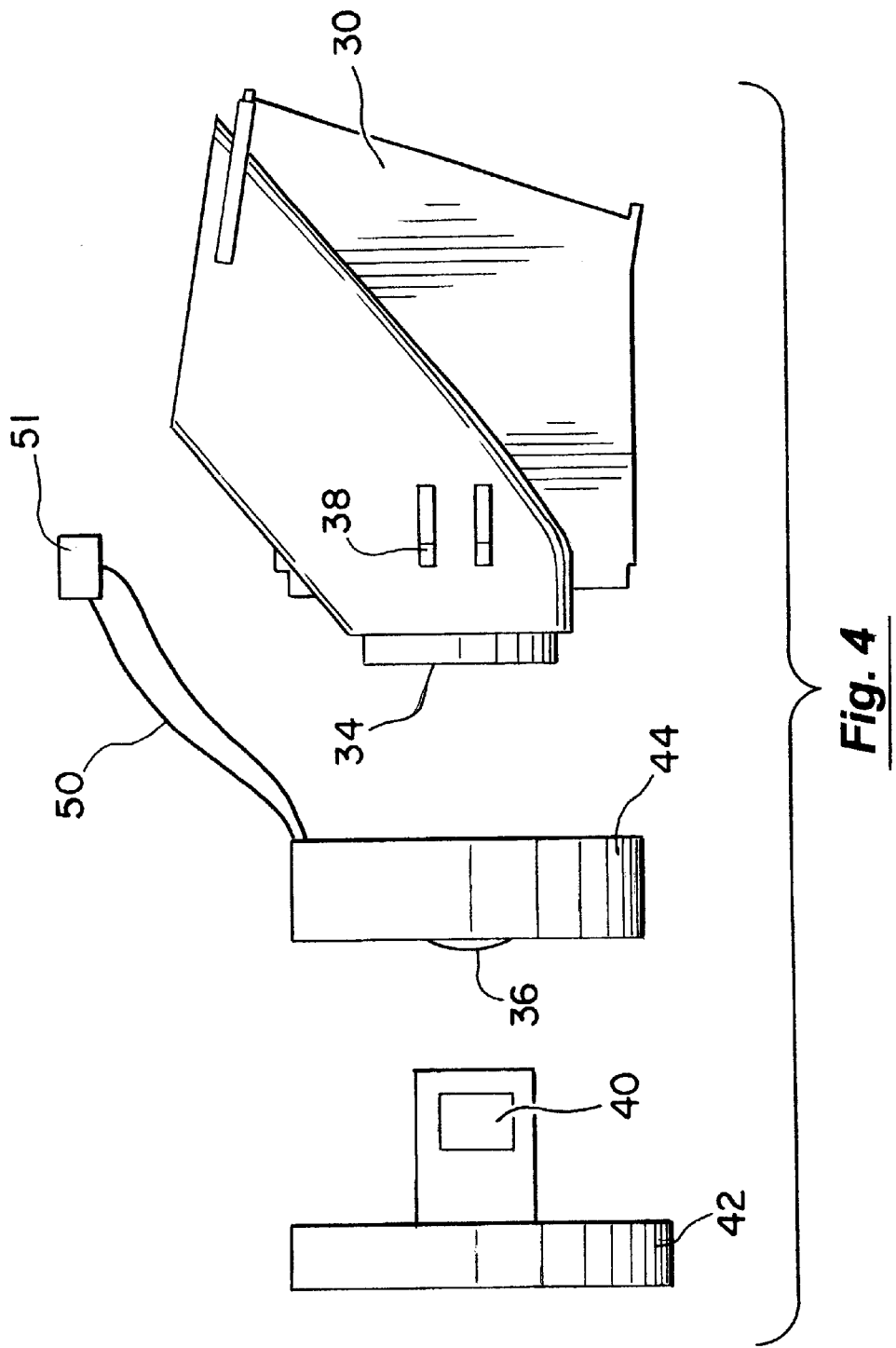
FIG. 4 is an exploded side of a vibrating element and a fluid receptacle.
Figure 5:
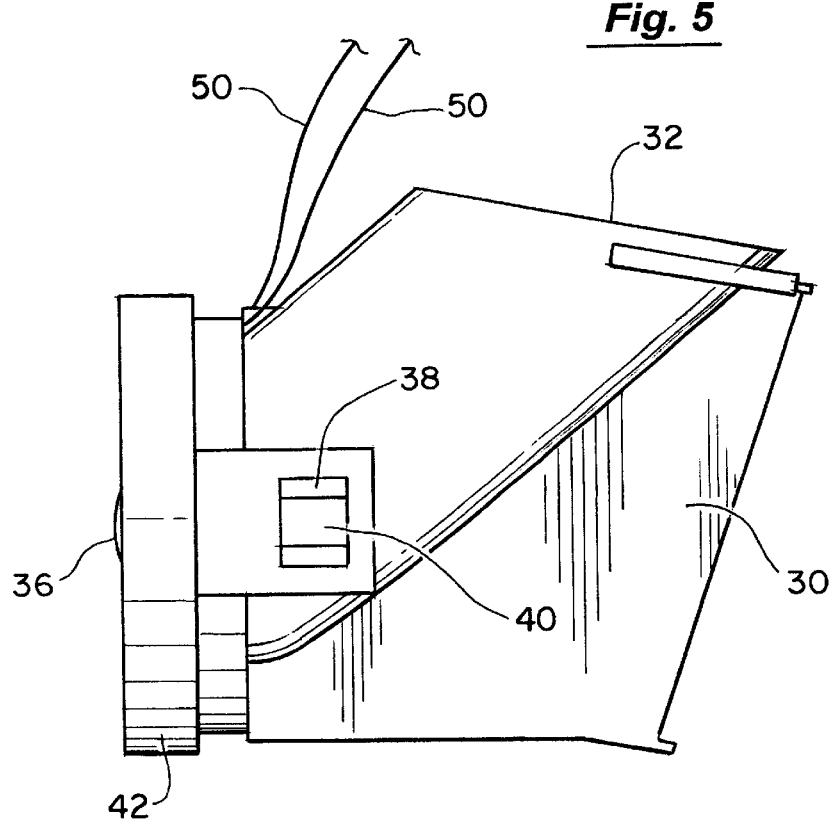
FIG. 5 is a side view of the vibrating element and fluid receptacle.
Figure 6:
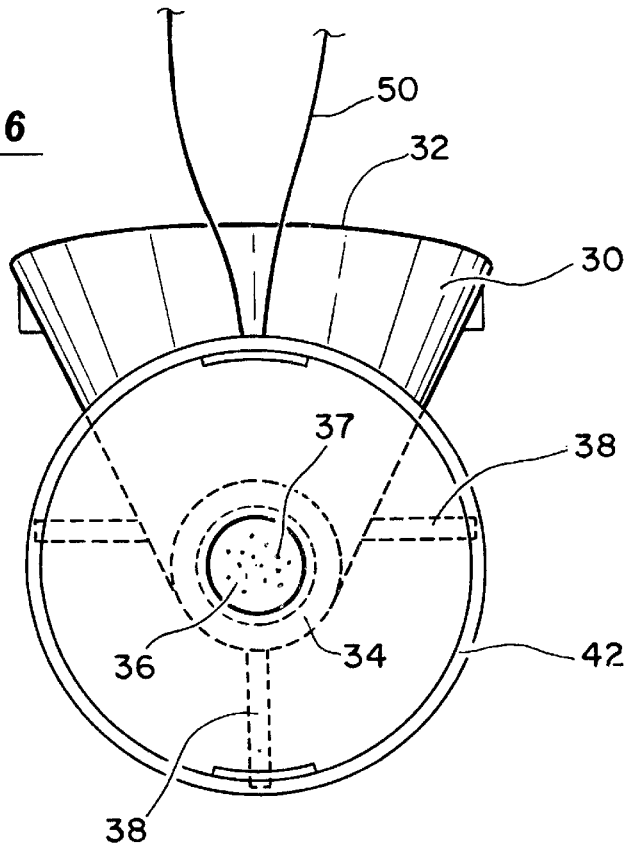
FIG. 6 is an end view of the assembly of FIG. 5.
Figure 7:
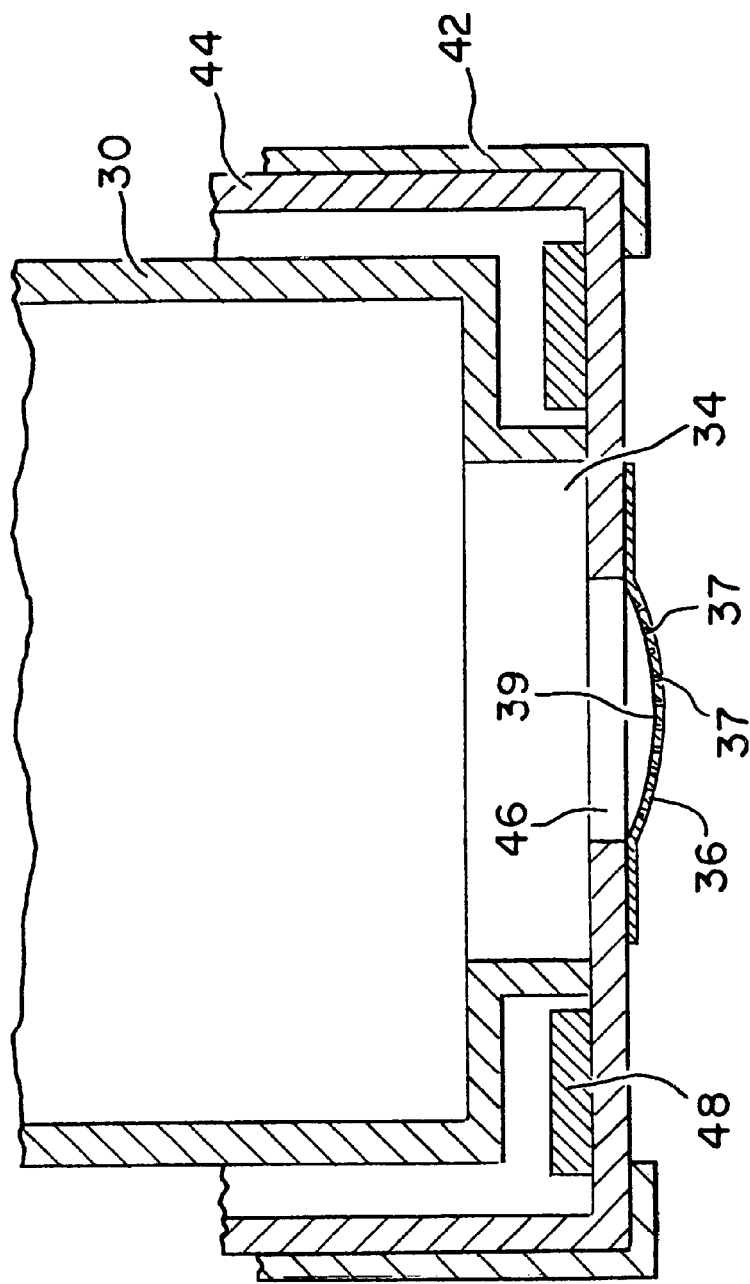
FIG. 7 is a cross-sectional view of an end of the assembly of FIG. 5 around line A—A.
Figure 8:
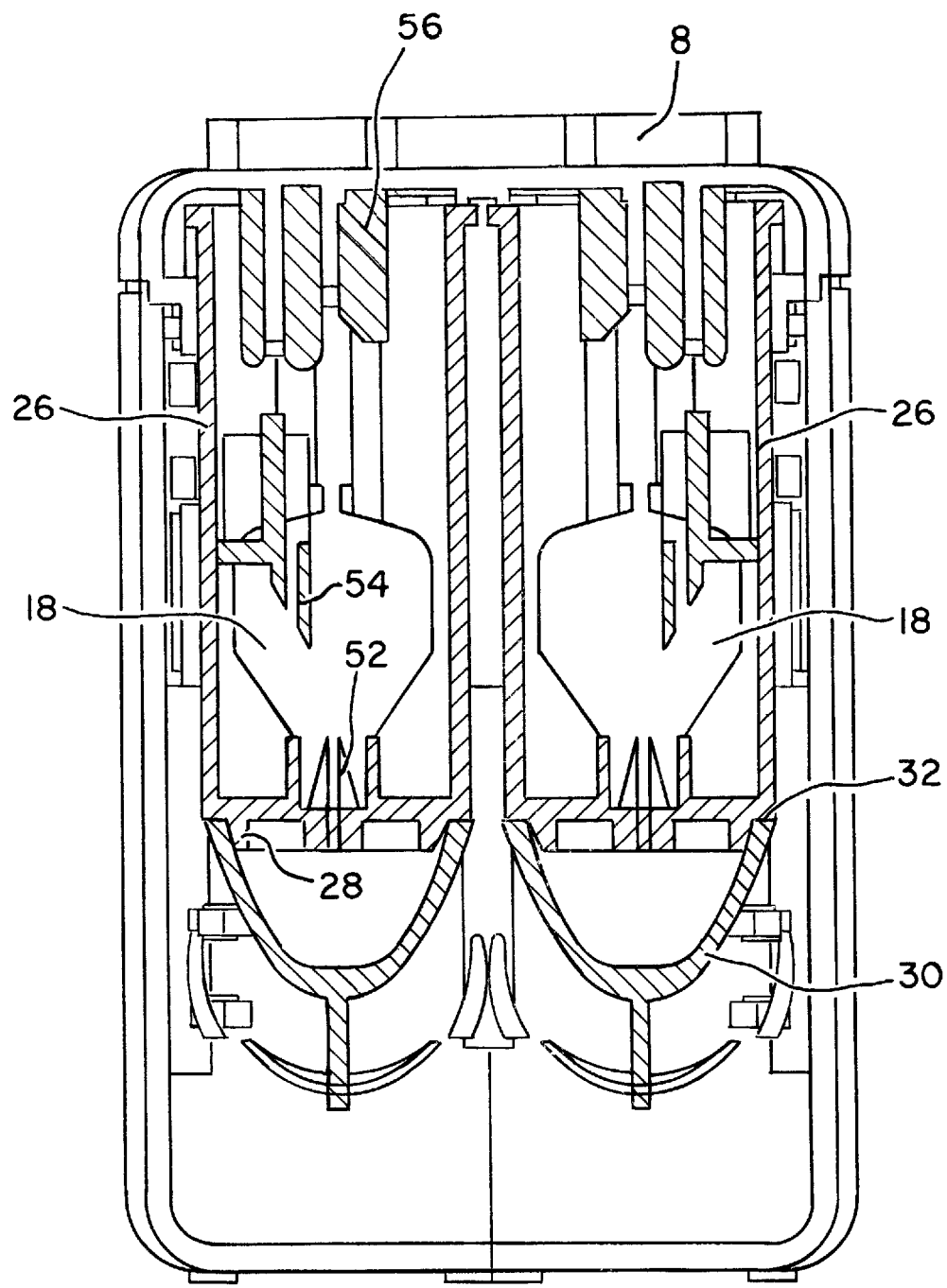
FIG. 8 is a partial cross-sectional view of the fluid delivery system for the device of FIGS. 3–7.

Referring to FIGS. 1 and 2, a nebulizing device 2 is shown. The nebulizing device 2 includes a housing 4 having a mouthpiece 6 and a door 8. The door 8 and mouthpiece 6 are removed in FIG. 2. The door 8 is coupled to the housing 4 with hinges 10 to open and close the door 8. As explained above, the nebulizing device 2 of the present invention may be used for a number of different applications and a preferred application is as a hand-held, portable device for delivery of at least one fluid to the lungs.

In one aspect of the invention, the nebulizing device 2 has at least two nebulizing elements 12. As will be described in greater detail below, the nebulizing elements 12 provide the ability to control the delivery of two different drugs to the patient. This can be important when two or more drugs are delivered to treat the same ailment. The drugs may be delivered at the same time or at different times in a controlled manner. The combination of nebulizing elements 12 also provides high flow rates when only a single drug is delivered with the nebulizing elements 12.

The fluid is contained in first and second fluid cartridges 14, 16. The fluid may be contained in any suitable container and a preferred container is an ampoule 18. The fluid may be delivered from the cartridges 14, 16 to the nebulizing elements 12 in any manner. A capillary feed system 20 and a system for delivering single doses are described below. The device 2 is designed so that the fluid cartridges 14, 16 can be replaced a number of times for subsequent use. It is understood that the fluid may be delivered in any other manner such as delivering a number of discrete volumes from a capsule using a piston.

The device 2 may be similar in construction and design to the devices described in U.S. Pat. No. 5,758,637 and U.S. Pat. No. 6,014,970, which are hereby incorporated by reference, although any other suitable structure may be used. The ampoule 18 preferably has a flange 22 which registers with slots 24 in the device 2. Fluid from the cartridge 14 is delivered to the nebulizing elements 12 with the capillary feed system 20 such as the capillary feed systems described in U.S. Pat. No. 5,938,117 and U.S. Pat. No. 5,758,637 which are incorporated here by reference.

Referring to FIGS. 3–8, another fluid delivery system is shown which is an alternative to the capillary system 20 described in connection with FIGS. 1 and 2. The system is designed to receive single dose ampoules 18 which are replaced after each use. The ampoule 18 fits within an adapter 26. The adapter 26 and ampoule 18 are preferably packaged together as a unit but may also be separate. The adapter 26 has a lip 28 which engages a fluid receptacle 30. The fluid receptacle 30 is large enough to accommodate the entire volume of the ampoule 18. In the preferred embodiment, the fluid receptacle 30 holds about 15 microliters to 2 milliliters and preferably about 500 microliters.

The fluid receptacle 30 is generally funnel-shaped and extends upward to an opening 32 which mates with the adapter 26. The fluid receptacle 30 has a second opening 34 which fits around a vibrating element 36. The vibrating element 36 has openings 37 therein and a back side 39 exposed to fluid in the fluid receptacle 30. Lateral tabs 38 extend from the receptacle 30 and engage an opening 40 in a holder 42. The vibrating element 36 is mounted around an opening 46 in a cup-shaped element 44 and the cup-shaped element is held within the holder 42. The vibrating element 36 has the apertures 37 through which fluid is expelled when the element 36 is vibrated. The receptacle 30 is preferably adhered to the element 36 with an adhesive such as silicone. The vibrating element 36 is vibrated with a ring-shaped piezoelectric member 48 mounted to the holder 42. Wires 50 connect the piezoelectric member 48 to a control system 51. The nebulizing element 12 may be any suitable device or structure and is preferably dome-shaped and manufactured in the manner described in U.S. Pat. No. 6,014,970 incorporated above.

The ampoule 18 is pierced by a first spike 52 which delivers fluid from the cartridge 14, 16 to the receptacle 30. The first spike 52 is mounted to the adapter 26 and is replaced with the adapter after each use. A second spike 54 introduces air into the cartridge 14, 16 as fluid is drained into the receptacle 30 for smooth delivery of the fluid. The first and second spikes 52, 54 automatically pierce the cartridge 14, 16 when the door 8 is closed. The second spike 54 is mounted to a top 56 which is driven into the receptacle 30 when the door 8 is closed. Although the fluid is delivered to the nebulizing element 12 in finite amounts or with capillary feed, the fluid may also be delivered to the nebulizing elements 12 in any other manner. For example, the fluid cartridge 14, 16 may contain a number of doses with the dose size being selected using conventional methods of delivering small amounts of fluid.

Figure 9:
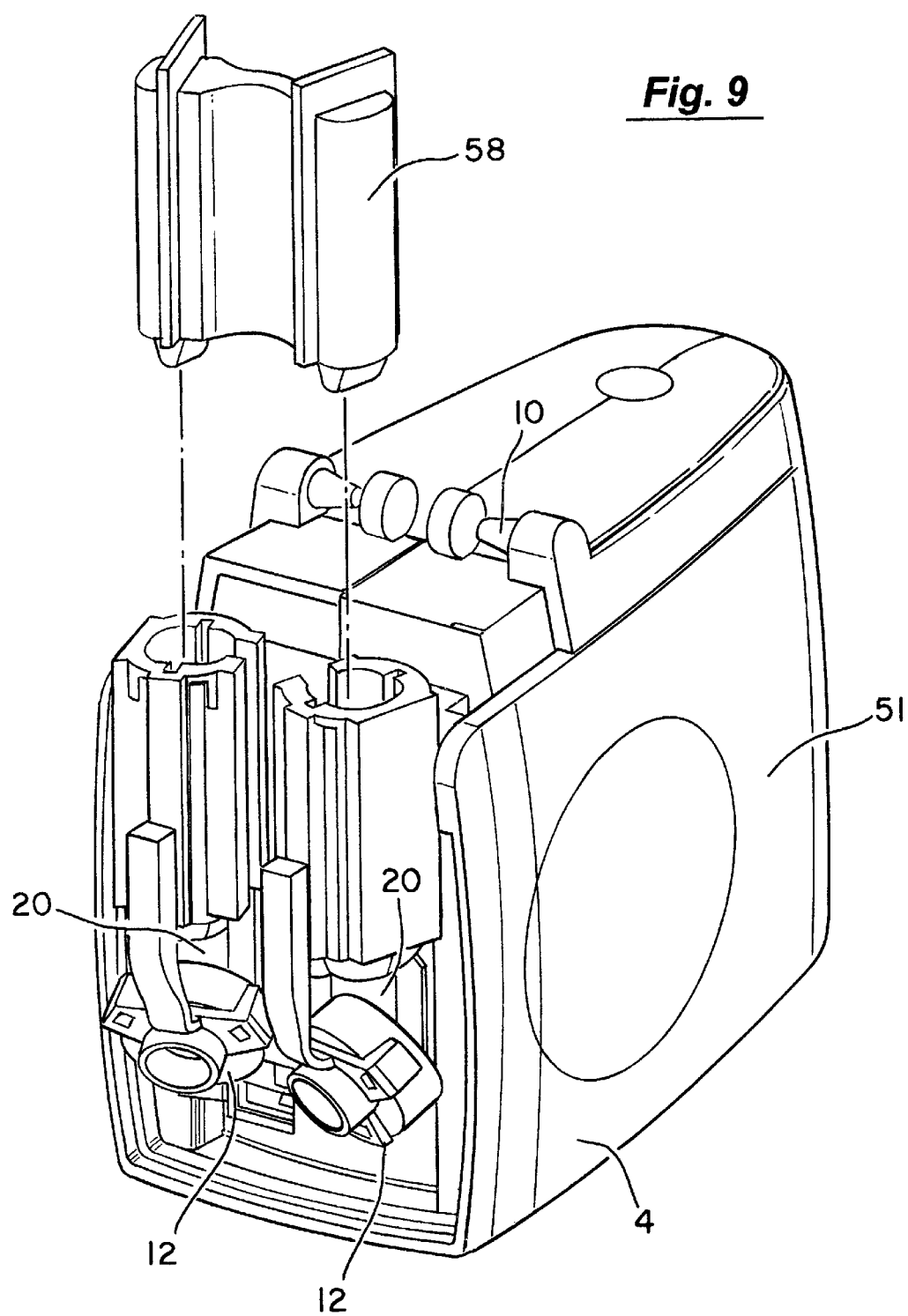
FIG. 9 shows a single fluid container.

Referring to FIG. 9, the device 2 may also have a single fluid cartridge 58. The fluid cartridge 58 may contain separate compartments for two different fluids. The fluid cartridge 58 may also simply contain a single fluid which is delivered to both nebulizing elements 12. When delivering only one fluid, the combination of nebulizers 12 provides the ability to produce large flow rates. For example, the nebulizing elements 12 may together be used to deliver 40–300 microliters, more preferably 100–250 microliters, in one breath. Stated another way, the nebulizing elements 12 are used to deliver at least 100 microliters and more preferably at least 200 microliters of fluid in one breath by the user. The nebulizing elements 12 also occupy a relatively small area so that the device is compact. The first and second nebulizers 12 also provide the ability to provide relatively large increases and decreases in fluid flow rate by simply activating or de-activating one or more of the nebulizers 12. Of course, the flow rate through each of the nebulizers may be adjusted by changing the power and/or frequency of operation.

The control system 51 controls the nebulizing elements and/or instructs the user on use of the device 2. The device has one or more indicators which may be audible or visual such as a clock, timer, or display which tells the user when and/or how to use the device. In a preferred embodiment, the indicator indicates one of more of the following: when the user should take a dose of one or more of the fluids, when the fluid is ready for inhalation, when the nebulizing element has been activated, and/or upon completion of a breath hold time. In one mode of operation, the indicator is simply a light. The user loads one or more cartridges 14, 16 and closes the door to deliver the fluid to the receptacle 30. When the dose is ready, the green light may flash which indicates that the user may activate the device 2. The device may be actuated with a button (not shown) or with a flow activated sensor. The light may remain on when the nebulizing element 12 has been activated and remains illuminated until a breath hold period is completed. The breath hold period may be set to be any value such as five seconds after completing delivery of the fluid. The visual indicators described herein are merely an example of a system for controlling and instructing the user in use of the device and many other variations for the control system may be used without departing from various aspects of the invention.

The device 2 may be operated in various other modes now described. Of course, the device 2 may operate in still different modes without departing from various aspects of the invention. In a first mode of operation, the first and second fluids may be delivered in the same breath or may be delivered independently. In a specific application of the present invention, the first fluid may contain a mucolytic, such as alpha domase, and the second fluid may contain an antibiotic, such as an aminoglycocide like tobramicin, or quinolone, pentamidine, or an antifungal such as amphotericin B. The control system 51 may also permit and prevent a set number of doses over a period of time. For example, the nebulizing device 2 may permit the user to have a set number of doses of the first fluid, such as six doses of the beta agonist per day, while permitting another set number of doses of the second fluid, such as two doses of the corticosteroid per day. In this manner, a single device 2 may be used to control the relative delivery of two different fluids.

The control system 51 may also operate to deliver the first and second fluids in the same breath. For example, the first fluid may be delivered before completing delivery of the second fluid. When operating in this mode, the first fluid may contain any suitable fluid such as a bronchodilator which opens the lungs in preparation for receiving the second fluid. The second fluid may be also delivered after the first or "main" fluid. The second fluid may be any suitable fluid such as a bronchorestrictor. Of course, the first and second fluids may be delivered simultaneously for a period of time without departing from the scope of the invention.

Finally, the control system 51 may operate to deliver different amounts of the first and second fluids in any of the modes described above. For example, the first fluid may be a short acting insulin and the second fluid may be a long acting insulin. The control system 51 may deliver different amounts of the two fluids such as twice as much short acting insulin as long acting insulin.

Figure 10:
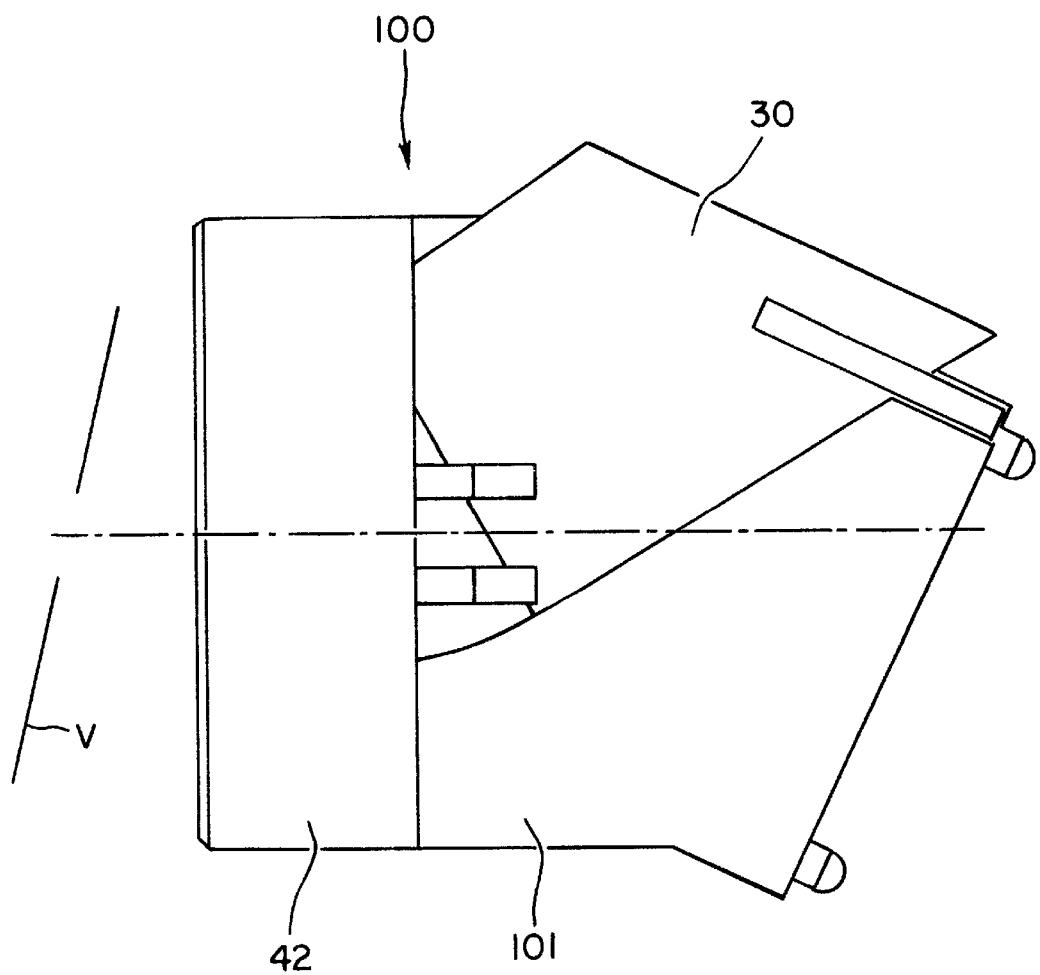
FIG. 10 is a side view of an assembly for nebulizing a fluid.
Figure 11:
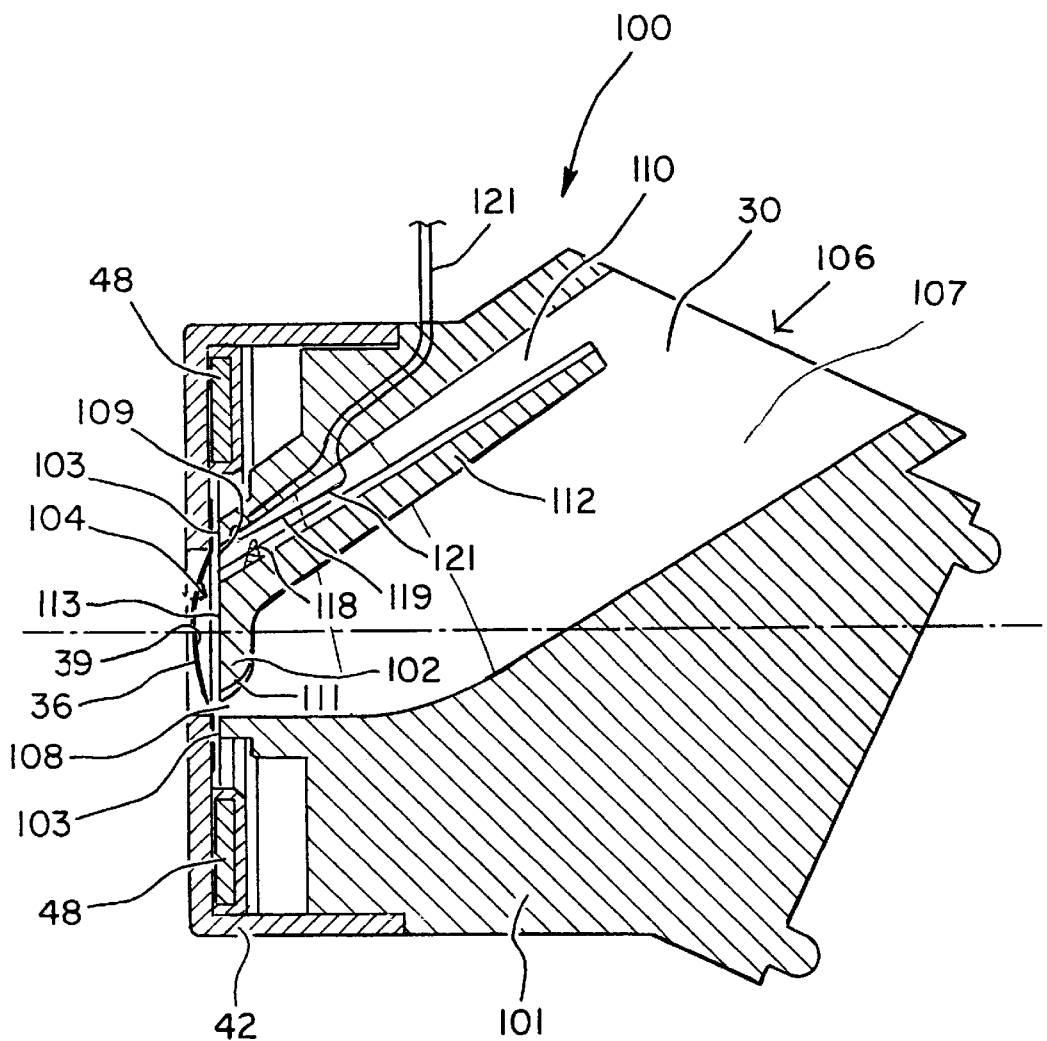
FIG. 11 is a cross sectional view of the assembly of FIG. 10 showing a flow directing element positioned adjacent a back side of a vibrating element.
Figure 12:
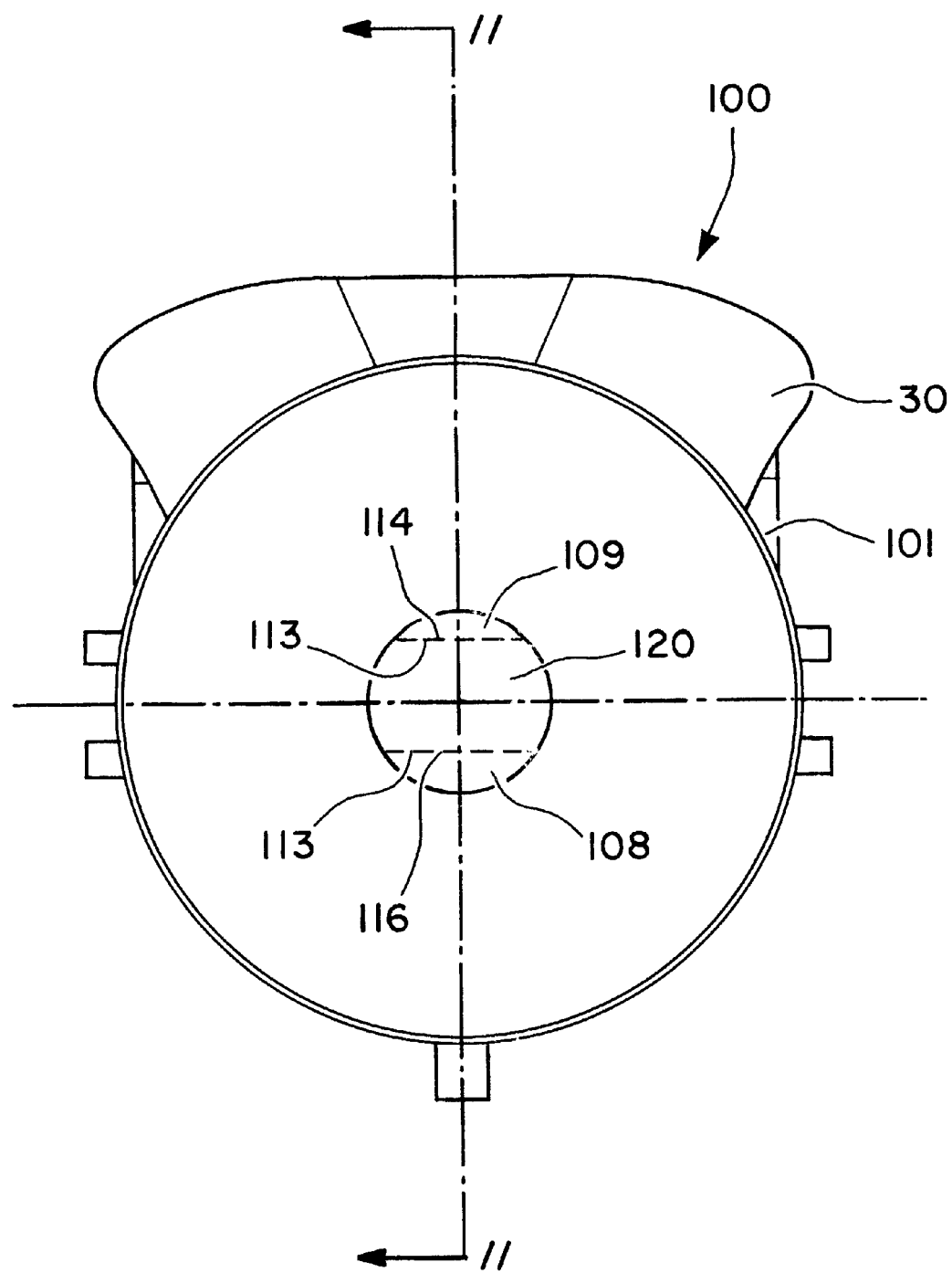
FIG. 12 is a front view of the assembly of FIGS. 10 and 11.

Referring to FIGS. 10–12, still another device 100 for nebulizing a fluid is shown wherein the same or similar reference numbers refer to the same or similar structure. Although the device 100, and the other devices described herein, are described in connection with a portable, handheld nebulizer, the device 100 may find uses in other fields without departing from many aspects of the present invention.

The device 100 has the vibrating element 36 which is preferably the hemispherical or dome-shaped element described above, however, the vibrating element 36 may take any other shape such as a flat plate, mesh or flexible membrane without departing from the invention. The vibrating element 36 is mounted inside a holder 42. A body 101 is mounted to the holder 42. The body 101 extends into the holder 42 and forms a seal 103 around the vibrating element 36 to contain the fluid in the manner described below. When the piezoelectric member 48 is activated, the vibrating element 36 vibrates so that fluid is ejected through apertures 37 in the vibrating element 36 as explained above. The device 100 may be substituted for any of the other devices or assemblies described above and discussion of the structure and use of such other devices described herein are specifically incorporated here.

A flow director 102 is positioned relatively close to the back side 39 of the vibrating element 36. In the preferred embodiment, the flow director 102 is positioned 0.003–0.015 inch, more preferably 0.003–0.030 inch and most preferably about 0.010 to 0.025 inch from the back side 39 of the vibrating element 36. A dispensing chamber 104 is defined between the vibrating element 36 and the flow director 102. The dispensing chamber 104 forms a relatively small volume of 2–30 microliters and more preferably 2–40 microliters.

A source of fluid 106, such as a reservoir 107, delivers fluid through an inlet 108 into the dispensing chamber 104. The size of the inlet 108 is relatively small to control the amount and/or rate of fluid which is delivered to the dispensing chamber 104. In a preferred embodiment, the inlet 108 has a size of 0.0015–0.0062 inches (squared) and more preferably about 0.0028 inch (squared). The source of fluid 106 may be any suitable source of fluid such as a multidose container, a single dose container or a capillary feed system. The source of fluid 106 may deliver the fluid to the dispensing chamber 104 through a tube or other conduit (not shown) without departing from various aspects of the invention. The flow director 102 is preferably a wall having a surface 113 facing the back side 39 of the vibrating element 36 and another surface 111 forming part of a fluid reservoir 107. Referring to FIG. 12, a plan view of the flow director 102 is shown in dotted-line position 113.

The flow director 102 directs any bubbles which may form in the dispensing chamber 104 away from the vibrating element 36. If a large amount of bubbles are formed, the bubbles can impede the flow of fluid from the vibrating element 36. The flow director 102 can also serve to trap and confine the bubbles before a large amount of bubbles can accumulating in the fluid receptacle 30. The flow director 102 generally isolates less than 10 percent and often less than 5 percent of the capacity of the receptacle 30. Bubbles which are generated naturally migrate upward through an outlet 109 which leads to an outlet chamber 110. The outlet 109 preferably has a size of 0.00388–0.00155 inch (squared) and more preferably about 0.0062 inch. The general configuration of the inlet 108 and outlet 109 can be seen in FIG. 12. The chamber 110 is preferably formed by a wall 112 which separates the chamber 110 from the remaining volume in the receptacle 30. The chamber 110 receives bubbles formed at the back side 39 of the vibrating element 36 which naturally migrate upwardly into the chamber 110. The chamber 110 may also have an active mechanism 119 for removing bubbles, such as a heating element or wire 121, or may simply have a passive element, such as a protrusion 118, which may help to coalesce and pop the bubbles entering the chamber 110.

Referring again to FIG. 10, the flow director 102 is oriented about 0–30 degrees, and preferably about 0–20 degrees, relative to vertical V when in use although other orientations may be used without departing from the invention. In another aspect of the invention, an upper portion 114 of the flow director 102 is positioned further from the back side 39 of the element 36 than a lower portion 116. The resulting geometry of the dispensing chamber 104 tends to move bubbles formed in the dispensing chamber 104 upward toward the outlet 109.

The flow director 102 may cooperate with the source of fluid 106 in any suitable manner. For example, the flow director 102 may receive the fluid through a lumen (not shown) leading to the inlet 114. In a preferred embodiment, the flow director 102 is formed by a wall 120 extending from lateral sides of the fluid receptacle 30. The wall 120 is relatively thin and is submerged in fluid in the fluid receptacle 30 when fluid is delivered. The fluid receptacle 30 preferably receives a volume of fluid that will be delivered through the vibrating element 36. The volume of fluid in the receptacle 30 passes through the inlet 114 into the dispensing chamber 104 where the fluid is expelled through the apertures in the vibrating element 36.

The invention has been described by way of the preferred embodiments, the invention should not be limited to the specific embodiments since various modifications and changes can be incorporated without departing from the scope of the invention. For example, the nebulizing elements may be relatively flat elements, the fluid container may be a titratable capsule, and the device may have three or more nebulizers. Finally, the invention has been described with respect to various features and aspects of the invention and it is understood that these features and aspects are independent of one another and none of the features or aspects should be considered essential or indispensable relative to the other features and aspects. For example, aspects of the fluid delivery system may be practiced with a device having only one nebulizing element and aspects of the multi-nebulizer device may be practiced with an entirely different fluid delivery system.

What is claimed is:

1. A method of nebulizing a fluid, comprising the steps providing a nebulizing device having a vibrating element with a plurality of apertures therein, the vibrating element having a back side and a front side, the nebulizing device also having a flow director, a dispensing chamber, an inlet and an outlet, the inlet and outlet leading to the dispensing chamber and the dispensing chamber being positioned between the flow director and the back side of the vibrating element;

delivering fluid through the inlet and into the dispensing chamber;

vibrating the vibrating element so that the fluid in the dispensing chamber which is at the back side of the vibrating element is ejected through the plurality of apertures in the vibrating element; and directing bubbles in the dispensing chamber away from the back side of the vibrating element with the flow director.

2. The method of claim 1, wherein:

the vibrating step is carried out with the outlet chamber receiving bubbles produced in the dispensing chamber.

3. The method of claim 1, wherein:

the vibrating step is carried out with the inlet being positioned below the outlet.

4. The method of claim 1, wherein:

the providing step is carried out with the inlet being positioned lower than the plurality of apertures and the outlet being positioned above the plurality of apertures.

5. The method of claim 1, wherein:

the providing step is carried out with the outlet chamber having means for popping bubbles which are produced in the dispensing chamber and migrate into the outlet chamber.

6. The method of claim 1, wherein:

the providing step is carried out with the dispensing chamber holding 2–30 microliters.

7. The method of claim 1, wherein:

the providing step is carried out with the dispensing chamber holding 2–20 microliters.

8. The method of claim 1, wherein:

the providing step is carried out with the source of fluid being a receptacle of fluid; and the method further comprises the step of delivering a volume of fluid to the receptacle before initiating the vibrating step.

9. The method of claim 8, wherein:

the vibrating step is carried out until the volume of fluid has been ejected through the plurality of apertures.

10. The method of claim 1, wherein:

the vibrating step is carried out with the flow director being at least substantially submerged in fluid when the vibrating step is initiated.

11. The method of claim 1, wherein:

the providing step is carried out with the flow director positioned 0.0030–0.030 inch from the back side of the vibrating element.

12. The method of claim 1, wherein:

the flow director has an upper end positioned further from the back side of the vibrating element than a lower end.

13. The method of claim 1, wherein:

the flow director is positioned at an angle relative to the back side of the vibrating element.

14. The method of claim 1, wherein:

the providing step is carried out with the vibrating element is mounted to a body having a mouthpiece for delivery of the fluid to lungs of a user.

15. A device for nebulizing a fluid, comprising:

a vibrating element having a plurality of apertures therein, the vibrating element having a front side and a back side, the plurality of apertures extending between the front and back sides;

a source of fluid;

an inlet which receives fluid from the source of fluid;

a flow director spaced apart from the backside of the vibrating element;

a dispensing chamber defined between the flow director and the back side of the vibrating element.

16. The device of claim 15, further comprising:

an outlet which is fluidly coupled to the dispensing chamber; and means for popping bubbles which pass through the outlet.

17. The device of claim 16, wherein:

the bubble popping means includes an outlet chamber which receives bubbles passing through the outlet.

18. The device of claim 16, wherein:

the inlet is positioned below the outlet.

19. The device of claim 15, wherein:

the flow director is positioned 0.003–0.030 inch from the back side of the vibrating element.

20. The device of claim 15, wherein:

the flow director is positioned 0.003–0.015 inch from the back side of the vibrating element.

21. The device of claim 15, wherein:

the flow director is configured to move bubbles away from the back side of the vibrating element.

22. The device of claim 15, wherein:

the vibrating element has a domed shape.

23. The device of claim 15, wherein:

the vibrating element is mounted to a body having a mouthpiece for delivery of the fluid to lungs of a user.

24. The device of claim 15, wherein:

the vibrating element is oriented about 0–20 degrees from vertical during operation; and the chamber is positioned at an upper end of the vibrating element during operation so that the bubbles naturally migrate upward and into the chamber.

25. The device of claim 15, wherein:

the vibrating element is oriented 0–20 degrees from vertical during operation; and the flow director is angled so that an upper end of the flow director is further from the back side of the vibrating element than a lower end.

26. The device of claim 15, wherein:

the inlet has a size of about 0.0015 inches (squared) to about 0.0062 inches (squared).

* * * * *